(12) United States Patent
Huwer et al.

(10) Patent No.: US 9,274,037 B2
(45) Date of Patent: Mar. 1, 2016

(54) METHOD AND COMPUTERIZED TOMOGRAPHY SYSTEM FOR DETERMINING BONE MINERAL DENSITY VALUES

(71) Applicant: SIEMENS AKTIENGESELLSCHAFT, Munich (DE)

(72) Inventors: Kerstin Huwer, Erlangen (DE); Bernhard Krauβ, Burgthann (DE); Michael Scheuering, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 101 days.

(21) Appl. No.: 14/029,934

(22) Filed: Sep. 18, 2013

(65) Prior Publication Data

US 2014/0086383 A1    Mar. 27, 2014

(30) Foreign Application Priority Data

Sep. 27, 2012    (DE) .......................... 10 2012 217 555

(51) Int. Cl.
*G01N 9/24*    (2006.01)
*G01N 23/04*    (2006.01)
(Continued)

(52) U.S. Cl.
CPC .. *G01N 9/24* (2013.01); *A61B 6/03* (2013.01); *A61B 6/482* (2013.01); *A61B 6/505* (2013.01);
(Continued)

(58) Field of Classification Search
CPC ....... G01N 9/24; G01N 23/046; A61B 6/583; A61B 6/505; A61B 6/5211; A61B 6/03; A61B 6/482; A61B 6/488; G06T 11/005; G06T 2211/408; G06T 2207/30008

USPC .................................................. 378/5, 54, 55
See application file for complete search history.

(56) References Cited

U.S. PATENT DOCUMENTS 5,809,104 A  *  9/1998  Kullenberg et al. ............ 378/54
5,864,146 A  *  1/1999  Karellas ............... A61B 6/4258
                                              250/581
(Continued)

FOREIGN PATENT DOCUMENTS

DE          69620869 T2      6/2003
DE       102004033989 A1     2/2006
(Continued)

OTHER PUBLICATIONS

Kalender Willia. et al.: "The European Spine Phantom—a tool for standardization and quality control in spinal bone mineral measurements by DXA and QCT", in: Eur.J.Radiol., 1995, vol. 20, pp. 83-92; US.

(Continued)

*Primary Examiner* — Jack Berman
(74) *Attorney, Agent, or Firm* — Harness, Dickey & Pierce, P.L.C.

(57) ABSTRACT

A method is disclosed for determining bone mineral density values of an object. In an embodiment, the method includes acquisition of first two-dimensional projection overview image data of the object to be examined in an image detail with a first X-ray energy; acquisition of at least second two-dimensional projection overview image data of the object to be examined in an image detail with at least one different second X-ray energy; determining a bone overview image data record using the first and second projection overview image data; determining at least one specific evaluation region of the image detail using the bone overview image data record; and determining a bone mineral density value for the specific evaluation region of the image detail using the image data of the bone overview image data record in the specific evaluation region. A computerized tomography system for implementing a method is also disclosed.

18 Claims, 5 Drawing Sheets

(51) Int. Cl.
  *G06T 11/00* (2006.01)
  *A61B 6/03* (2006.01)
  *A61B 6/00* (2006.01)

(52) U.S. Cl.
  CPC ............... *A61B 6/5211* (2013.01); *A61B 6/583* (2013.01); *G01N 23/046* (2013.01); *G06T 11/005* (2013.01); *A61B 6/488* (2013.01); *G06T 2207/30008* (2013.01); *G06T 2211/408* (2013.01)

(56) References Cited

U.S. PATENT DOCUMENTS

| | | | |
|---|---|---|---|
| 7,583,779 B2 * | 9/2009 | Tkaczyk et al. | 378/4 |
| 8,548,118 B2 * | 10/2013 | Hsieh et al. | 378/16 |
| 2004/0101093 A1 | 5/2004 | Matsumoto | |
| 2006/0013361 A1 | 1/2006 | Fehre et al. | |
| 2010/0014737 A1 | 1/2010 | Ruhrnschopf et al. | |
| 2010/0040268 A1 | 2/2010 | Boeing et al. | |

FOREIGN PATENT DOCUMENTS

| | | |
|---|---|---|
| DE | 102008030552 A1 | 12/2009 |
| DE | 102008037347 A1 | 2/2010 |

OTHER PUBLICATIONS

DVO Guideline Osteoporosis 2009; www.dv-osteologie.org/dvo_leitlinien/dvo-leitlinie-2009; www.schattauer.de/fileadmin/assets/zeitschriften/osteologie/0111_OST_01_2011.pdf; pp. 55-74.

Didier H. et al; "How can we measure bone quality?"; Baillière's Clinical Rheumatology; vol. 11; No. 3; pp. 495-515; ISBN: 0-7020-2320-5; 1997.

Clinical Application 1; Application Guide; Software Version syngo CT 2005A; pp. 34-48; http://www.healthcare.siemens.com.

Meeting Report, "WHO Scientific Group on the Assessment of Osteoporosis at Primary Health Care Level", Brussels, Belgium, May 5, 2004, pp. 1-13.

* cited by examiner

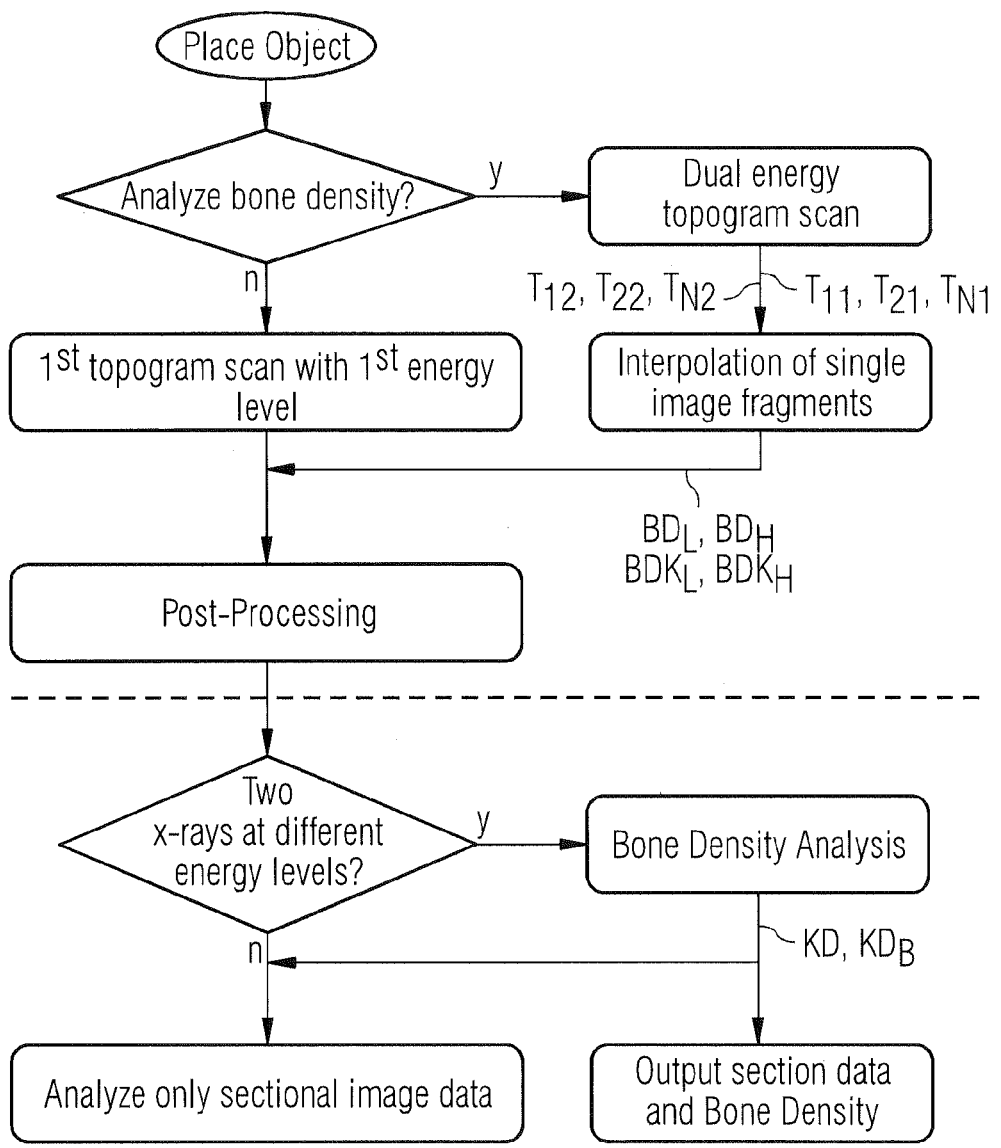

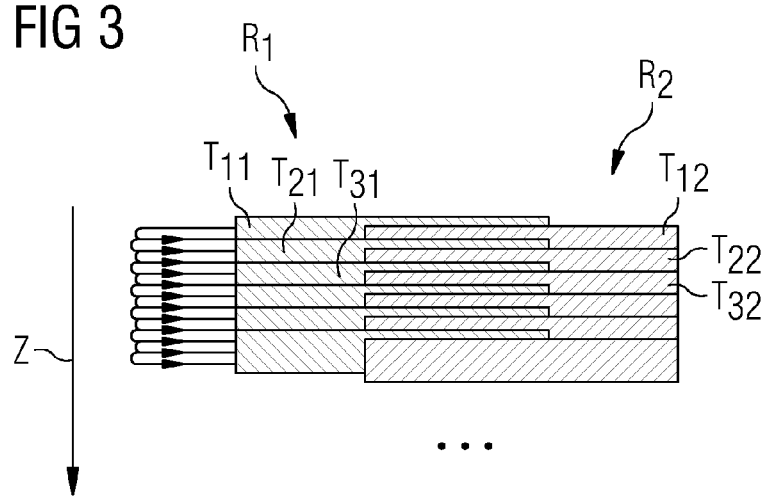
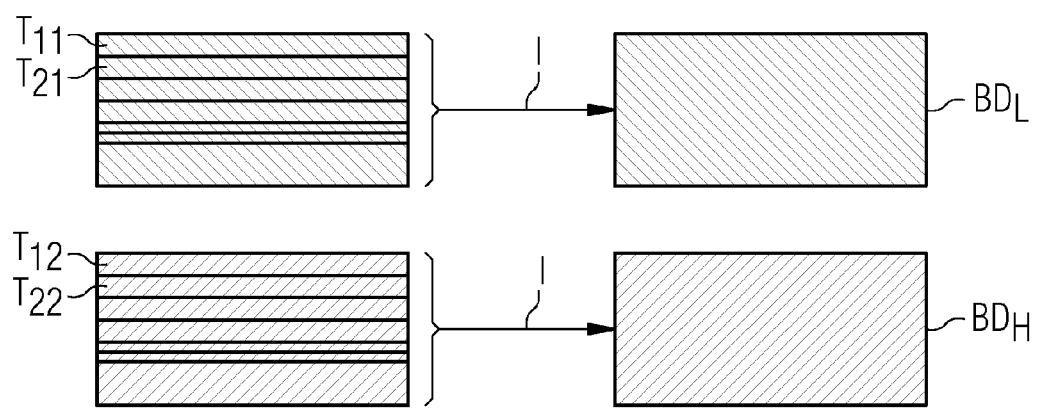

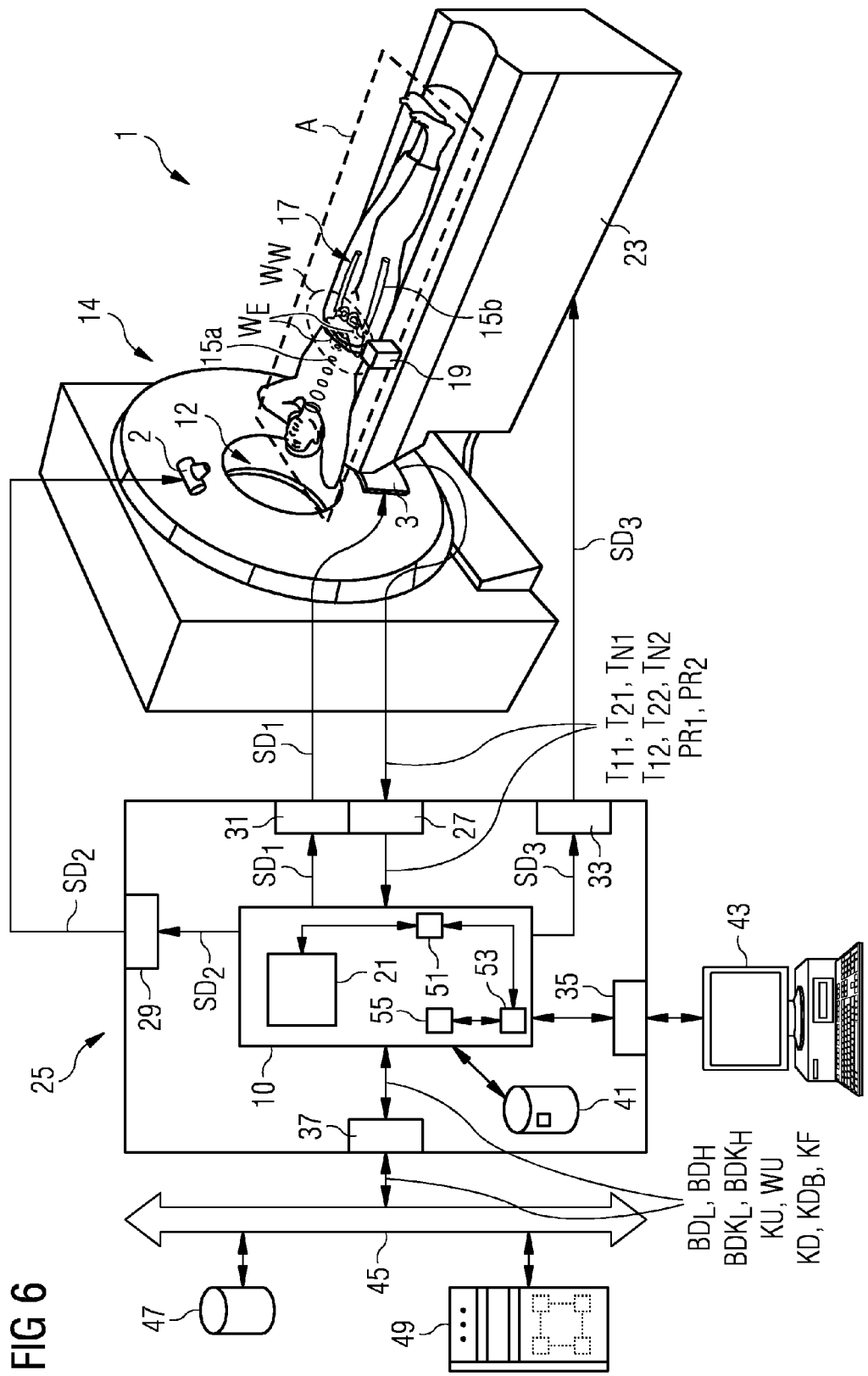

METHOD AND COMPUTERIZED TOMOGRAPHY SYSTEM FOR DETERMINING BONE MINERAL DENSITY VALUES

PRIORITY STATEMENT

The present application hereby claims priority under 35 U.S.C. §119 to German patent application number DE 102012217555.5 filed Sep. 27, 2012, the entire contents of which are hereby incorporated herein by reference.

FIELD

At least one embodiment of the invention generally relates to a method for determining bone mineral density values of an object to be examined by way of a computerized tomography system. At least one embodiment of the invention also generally relates to a computerized tomography system for carrying out a method of this kind.

BACKGROUND

X-ray radiation is used to depict the interior condition and structure of three-dimensional and non-transparent objects to be examined. An object to be examined can be an animate body, i.e. a human or animal. Inanimate objects, such as tires, welded joints or other industrial products may also be scanned, however, for the purpose of materials testing or quality control of manufacturing processes using X-ray systems. An excessive dose of X-ray radiation has proven to be harmful to living organisms since it may damage tissue irreparably and can have a carcinogenic effect. In terms of the patient attempts are therefore being made to reduce the exposure to radiation by way of an ongoing improvement in radiographic scanning devices and by way of limitation to necessary X-ray images.

A plurality of radiography scans of people and animals are often made in an uncoordinated fashion using different scanning devices, wherein the same region of the body is often irradiated several times. A DXA/DEXA (dual energy X-Ray Absorptiometry) examination by way of example for the purpose of bone density analysis is also indicated in some cases for patients who are given a computerized tomography scan in the region of the spine, the abdomen or the femoral head. The repeated and potentially uncoordinated production of X-ray images by way of different scanning devices leads to high exposure to radiation and considerable expenditure in terms of time and cost for the test persons.

SUMMARY

At least one embodiment of the present invention is directed to developing a method for determining bone mineral density values with respect to a reduction in the exposure to radiation for the test person and a speeding up of the measuring process.

A method and a computerized tomography system are disclosed.

At least one embodiment of the inventive method includes at least the following steps:
acquisition of first two-dimensional projection overview image data of the object to be examined in an image detail with a first X-ray energy,
acquisition of at least second two-dimensional projection overview image data of the object to be examined in an image detail with at least one second X-ray energy which differs from the first X-ray energy,
determining a bone overview image data record using the first projection overview image data and the second projection overview image data,
determining at least one specific evaluation region of the image detail using the bone overview image data record,
determining a bone mineral density value for the specific evaluation region of the image detail using the image data of the bone overview image data record in the specific evaluation region.

In addition to a conventional acquisition unit for the acquisition of first and second two-dimensional projection overview image data of the object to be examined in an image detail with said first and second X-ray energy, at least one embodiment of an inventive computerized tomography system for carrying out at least one embodiment of the invention has a bone overview determination unit for determining a bone overview image data record using the first projection overview image data and the second projection overview image data. The computerized tomography system also has an evaluation region determination unit for determining at least one specific evaluation region of the image detail using the bone overview image data record and a mineral density value determination unit for determining a bone mineral density value for the specific evaluation region of the image detail using the image data of the bone overview image data record in the specific evaluation region.

The majority of the components of at least one embodiment of the inventive CT system, in particular the bone overview determination unit, the evaluation region determination unit and the mineral density value determination unit, can also be designed as software modules for example on a controller and/or image generating unit of a CT system. An implementation largely in software of at least one embodiment of the inventive method has the advantage that existing computerized tomography systems can be easily upgraded by a software update to operate inventively. In this respect the object is also achieved by a computer program product which can be loaded directly into a memory of a programmable controller and/or an image generating unit of a computerized tomography system with program code means to execute all steps of at least one embodiment of the inventive method if the program product is executed on the controller and/or image generating unit.

BRIEF DESCRIPTION OF THE DRAWINGS

The invention will be explained once again in more detail below with reference to the accompanying figures and with the aid of exemplary embodiments. Identical components are provided with identical reference numerals in the various figures, in which:

FIG. 2 shows a flowchart of determination of bone mineral density values of an object to be examined according to a second embodiment, FIG. 3 shows a schematic detailed sketch relating to obtaining low-energy and high-energy overview image partial data records in a method according to FIG. 2, FIG. 4 shows a schematic detailed sketch of the processing of the overview image partial data records to form a low-energy topogram and a high-energy topogram, FIG. 6 shows a schematic image of a computerized tomography system.

DETAILED DESCRIPTION OF THE EXAMPLE EMBODIMENTS

Figure 1:
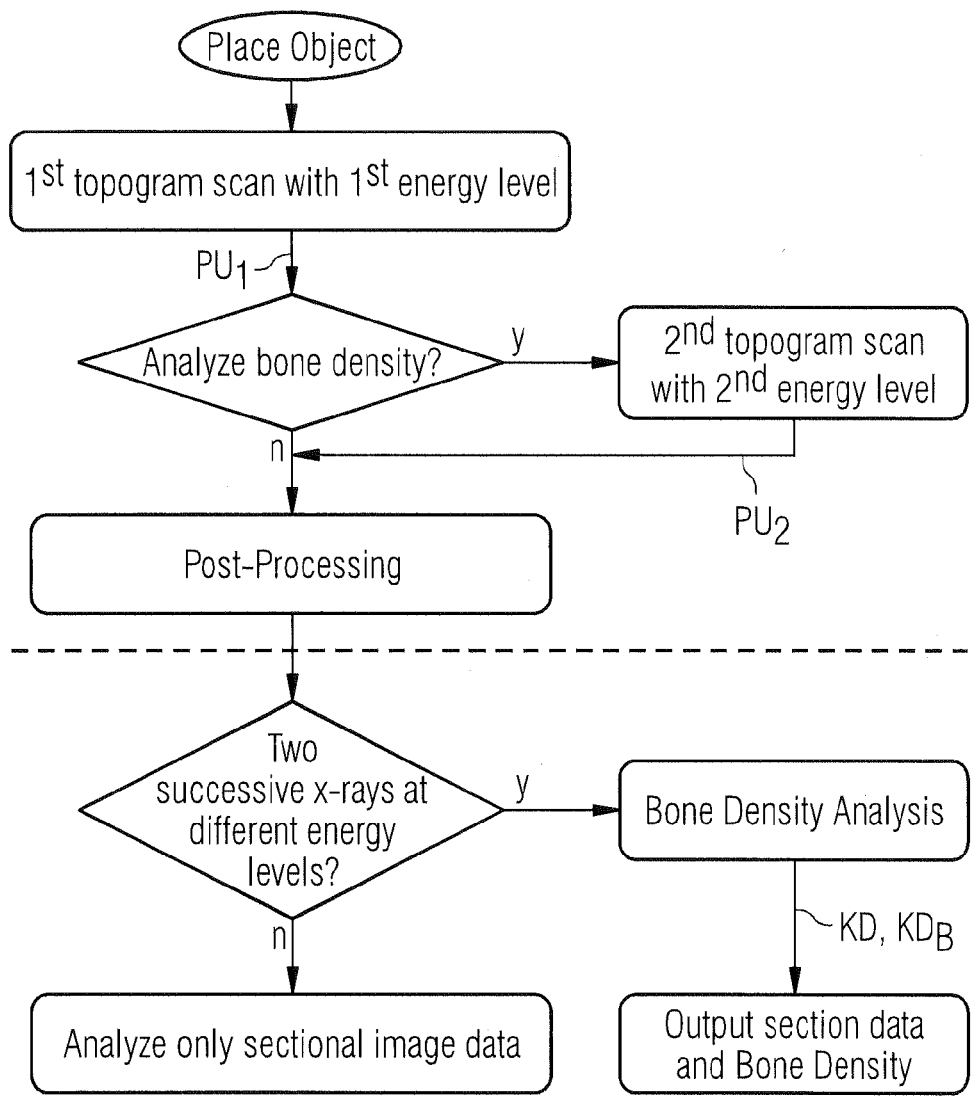
FIG. 1 shows a flowchart of determination of bone mineral density values of an object to be examined according to a first embodiment.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the inventive method includes at least the following steps:

acquisition of first two-dimensional projection overview image data of the object to be examined in an image detail with a first X-ray energy, acquisition of at least second two-dimensional projection overview image data of the object to be examined in an image detail with at least one second X-ray energy which differs from the first X-ray energy, determining a bone overview image data record using the first projection overview image data and the second projection overview image data, determining at least one specific evaluation region of the image detail using the bone overview image data record, determining a bone mineral density value for the specific evaluation region of the image detail using the image data of the bone overview image data record in the specific evaluation region.

In at least one embodiment, the method steps are preferably executed in the sequence in which they are given, wherein the first and second two-dimensional projection overview image data can be acquired in any desired sequence or simultaneously. At least one embodiment of the method can also include intermediate steps which are not described and/or are not described in detail in the description.

The computerized tomography system (hereinafter also called a CT system) is a device for producing sectional images of an object to be examined by way of X-ray radiation. The X-ray radiation emitted by an X-ray source penetrates through the object to be examined placed in a measuring space to different extents and is measured by a detector arrangement on a side of the measuring space opposing the X-ray source. During a measuring process X-ray source and detector arrangement rotate in a circle and at high speed around the measuring space. Sectional images and/or 3D volume data can be reconstructed by way of a computer-based evaluation of a large number of X-ray projections of an object to be examined taken from different directions.

Within the scope of at least one embodiment of the invention, the image detail is to be taken to mean a partial area of the object to be examined which is penetrated by X-ray radiation to obtain measurement data. The object to be examined can, as mentioned, be for example a living or dead body of a person or animal or be part of a body which surrounds it, wherein the object to be examined has a bone portion, for example as part of a skeleton. The image detail can include any desired part of the object to be examined, for example a human torso from the chest to the thigh, or a wrist. The image detail preferably includes the entire extent of the object to be examined, however.

Within the scope of at least one embodiment of the invention "projection overview image data" designates the X-ray radiation intensity values measured by the detector arrangement in the case of a fixed angular position of the X-ray source on the detector arrangement, and these conventionally vary as a function of the thickness and the absorption properties of the object to be examined. To produce an overview image there is as a rule a (continuous or sequential) relative movement of the object to be examined with respect to the X-ray source or detector arrangement in an advance direction, which conventionally runs parallel to a length direction of the object to be examined. This depends on the width of the detector in the advance direction and on the desired extent of the overview images in this direction.

In contrast to the conventional imaging method of CT projection measurement data for the reconstruction of three-dimensional image data or sectional images, X-ray source and detector arrangement do not rotate around the measuring space in this case but remain stationary at an angular position, by way of example with the X-ray source above the object to be examined, to produce a frontal projection, or with the X-ray source in a lateral position to produce a sagittal projection. Irrespective of the fact that data potentially produced along the direction of movement is placed on each other to produce a complete overview image, this projection overview image data can consequently be used directly and without reconstruction as projection images. The projection overview image data accordingly already forms a two-dimensional image like a simple X-ray image. Such projection overview image data is conventionally completed before measurements of individual slices of an object to be examined are made using the computed tomographs in order to produce a topogram, with the aid of which further images may then be planned. A method for producing a topogram of this kind is disclosed in DE 10 2008 037347 A1, the entire contents of which are hereby incorporated herein by reference.

Measurements in which image data records of the object to be examined are made with two or several different X-ray energies are conventionally called "dual energy methods" or "multiple energy" methods. The term "energy" of X-ray radiation (hereinafter also called "X-ray energy" or "X-ray radiation energy") is in this connection taken to mean energy distribution or rather the energy spectrum. The energy spectrum of the X-ray radiation emitted by an X-ray tube is dependent on the applied tube voltage. It is represented by a value of the X-ray energy which conventionally forms a maximum or a mean of the energy spectrum. The X-ray energy is conventionally given as the voltage value of the tube voltage set at the X-ray tube. Since the attenuation of the X-rays in the various materials is dependent on the X-ray energy, using the "dual energy method" or the "multiple energy" method it is possible to obtain additional information compared to a measurement using only one X-ray energy.

The at least first and second X-ray energy used to obtain the first and second projection overview image data are distinguished according to the "dual energy method" preferably by a high energy separation. A voltage between 70 kV and 100 kV is frequently applied to produce a low-energy X-ray energy spectrum at an X-ray tube, whereas a tube voltage between 120 kV and 150 kV is selected to produce a, relative to the first X-ray energy, high-energy X-ray energy spectrum. The first X-ray energy is preferably low-energy (for example 80 kV) and the second X-ray energy high-energy relative thereto (for example 140 kV) or vice versa.

The bone overview image data record preferably substantially includes information on outlines, thickness and material quality of the portions of bone captured in the image detail of the preferably human or animal object to be examined. The information can be displayed for example by means of gray scale graduation and/or color coding and thus be made discernible to the operator. The image detail of the overview image data records can be identical to the image detail of the first and second projection overview image data or be smaller.

The bone overview image data record can be produced by way of example by an image processing method which is based on a weighted subtraction of projection overview data and enables an elimination of soft tissue structures of the object to be examined. Soft tissue image data, for example of muscles, tendons or fat, are subtracted or removed in a specific weighting from the projection overview image data. In the case of a person or animal the bone overview image data record can include the contours of a skeleton or partial skeleton. Calcium is preferably used as the basic material for calculation of the bone overview image data record since the calcium content in the bone material is usually particularly high. Calculation of the bone overview image data record offers the advantage of a precise depiction of possible evaluation regions which can be used in the following steps to determine the bone mineral density value.

According to a preferred embodiment of the method, as an alternative to this approach the bone overview image data record can be calculated by applying a two-dimensional function which directly allocates an areal density value of the bone to the measured attenuation in the high- and low-energy projection overview image data. This simplifies subsequent determination of a bone mineral density value for the specific evaluation region since it is then not imperative for additional calibration functions to be determined.

The specific evaluation region within the image detail in each case includes image data from a portion of bone. It can include further evaluation regions, i.e. smaller evaluation areas in each case, which therefore form sections of the first evaluation region. Additional evaluation regions are in each case isolated in accordance with the purpose of greater significance with respect to determination of the bone mineral density value. In the case of a human or monkey a first evaluation region preferably includes a left and/or right neck of the femur (femoral neck) and/or the lumbar spine, particularly preferably the first three or four joints of the lumbar spine. As is known, these skeletal regions prove to be particularly significant in the determination of the bone mineral density value. The step of determining the first evaluation region and optionally further, more narrowly defined evaluation regions can be independently carried out according to defined criteria and sequences by the X-ray system and/or be controlled in various intermediate steps by the operator, by way of example by way of input via a graphic user interface.

The bone mineral density value indicates in what concentration a specific mineral, for example calcium or magnesium, is present in a bone or bone segment. The bone mineral density value is determined in the evaluation region or in the smallest determined evaluation area of the bone overview image data record. The bone mineral density value is in this connection preferably defined as a quantity of calcium hydroxylapatite per unit of area in the evaluation region since this calcium compound indicates a bone mineral density value particularly informatively.

At least one embodiment of the inventive method may prove to be particularly advantageous for example within the framework of a more extensive imaging examination by way of a computed tomograph. According to the current prior art, as mentioned, a two-dimensional overview image (topogram) of the object to be examined or of a patient is routinely made for the purpose of planning a tomography scan. If the conceptual interest, which forms the basis of the performance of the tomography scan and can include for example obtaining a detailed image of a bone fracture, also includes determining a bone mineral density value of the patients, then according to the inventive method a second topogram can be taken using a different X-ray energy, so a bone mineral density value can be determined from the dual energy topogram obtained.

Within the scope of at least one embodiment of the invention, the same measured projection overview image data can simultaneously be used accordingly to plan a CT examination and to determine a bone mineral density value. Compared to a conventional CT examination and an additional conventional measurement of a bone mineral density value by means of a DXA/DEXA scanner the inventive method therefore reduces the total radiation exposure of the patient in the case of the same technical characteristics of the devices used by the amount of X-ray radiation required for a single radiography image. Since the measuring time for taking the second topogram is only a few seconds, a further advantage results of a considerable time reduction for a patients on whom the two measurements are being taken.

That a separate DXA/DEXA device is no longer required in a radiological practice if a computerized tomography system is available is also a particularly advantageous effect. This saves the operator of the practice considerable acquisition and maintenance costs and signifies a further reduction in time outlay for the patient since both examinations can be carried out in a single practice. Compared with the further alternative methods of a three-dimensional measurement of the bone mineral density by means of quantitative computerized tomography the inventive method in turn provides the advantage of lower radiation exposure of the test person since only a single acquisition of X-ray projection data is carried out instead of a plurality of X-ray projections for the reconstruction of three-dimensional image data with a second X-ray energy. Furthermore, the two-dimensional measuring methods provide the advantages of reductions in energy and time.

In addition to a conventional acquisition unit for the acquisition of first and second two-dimensional projection overview image data of the object to be examined in an image detail with said first and second X-ray energy, at least one embodiment of an inventive computerized tomography system for carrying out at least one embodiment of the invention has a bone overview determination unit for determining a bone overview image data record using the first projection overview image data and the second projection overview image data. The computerized tomography system also has an evaluation region determination unit for determining at least one specific evaluation region of the image detail using the bone overview image data record and a mineral density value determination unit for determining a bone mineral density value for the specific evaluation region of the image detail using the image data of the bone overview image data record in the specific evaluation region.

The acquisition unit preferably includes an X-ray source (for example an X-ray tube) for the emission of X-ray radiation which is particularly preferably designed for a fast switchover between a first X-ray energy and a second X-ray energy, wherein the second energy differs from the first X-ray energy. In addition, as customary, it includes a detector arrangement for the acquisition of projection overview image data of an object to be examined, and during operation of the acquisition unit this is arranged in a measuring space.

The majority of the components of at least one embodiment of the inventive CT system, in particular the bone overview determination unit, the evaluation region determination unit and the mineral density value determination unit, can also be designed as software modules for example on a controller and/or image generating unit of a CT system. An implementation largely in software of at least one embodiment of the inventive method has the advantage that existing computerized tomography systems can be easily upgraded by a software update to operate inventively. In this respect the object is also achieved by a computer program product which can be loaded directly into a memory of a programmable controller and/or an image generating unit of a computerized tomography system with program code means to execute all steps of at least one embodiment of the inventive method if the program product is executed on the controller and/or image generating unit.

Further, particularly advantageously embodiments and developments of the invention result from the dependent claims and from the following description, wherein the independent claims of one claims category may also be developed analogously to the dependent claims of another claims category.

According to a preferred embodiment, the step of the inventive method in which the first and second projection overview image data is acquired includes the following steps:
    movement of the object to be examined relative to a measuring space of the computerized tomography system,
    switching over an X-ray source between the first X-ray energy and the second X-ray energy,
    acquisition of first projection overview image partial data records with the first X-ray energy and of second projection overview image partial data records with the second X-ray energy of the object to be examined in an image detail by means of a detector arrangement.

The image detail can be delimited by the dimensions of the field of view of the detector arrangement of the computed tomograph. It can be widened with respect to this field of view since during a measuring process the object to be examined is conventionally moved through the measuring space in an advance direction on a platform or the examination table and/or the measuring space is moved across the object to be examined.

The projection overview image data is acquired in the form of projection overview image partial data records. These projection overview image partial data records therefore each form a subset of a set of the projection overview image data, which was acquired with the first or second X-ray energy, since they only have the fraction of the area of the total image detail acquired by the detector arrangement at a specific time in each case. These projection overview image partial data records can be stored for example in a buffer and be merged in an image processing method to form the complete first and second projection overview image data.

A measuring process, i.e. acquisition of the first and second projection overview image data or the projection overview image partial data records can occur separately for each of the energies in one or two or more measuring cycles. In a first measuring cycle the object to be examined can by way of example conventionally lie on a platform of an examination table and from a starting position can be moved through the measuring space by means of the examination table whereas the computed tomograph, as described above, with a fixed angular position of X-ray source and detector carries out a scan (i.e. a measurement data acquisition) with the first X-ray energy and obtains first projection overview image data of the object to be examined in the process. From an end position of the examination table after the first measuring process the examination table can then be moved back into the starting position. A second measuring cycle can then take place which differs from the first measuring cycle only in the use of the second X-ray energy, by means of which second projection overview image data is generated. Alternatively, the second measuring cycle can also take place directly during the return of the examination table into the starting position.

To be able to subsequently process the projection overview image data produced with the different energies the image detail of the object to be examined and the position of the object to be examined should be optimally identical in both measuring cycles, so internal structures of the object to be examined are mapped in the two measuring cycles at identical pixels of the detector arrangement. During the movement relative to the measuring space the movements of the object to be examined are therefore particularly preferably reduced to a minimum.

According to a further example embodiment, the inventive method is configured in such a way that the acquisition of the first projection overview image partial data records and second projection overview image partial data records occurs by means of an alternate switchover between the first X-ray energy and the second X-ray energy.

The alternate switchover can preferably be made in short time intervals and several times during a topogram scan or measuring cycle. The switch between the two X-ray energies can occur by way of a switchover of the tube voltage and/or of the tube current applied at the X-ray source of the X-ray system. A method of this kind is known as "fast kVp/mA switching", wherein the switchover can happen within for example 0.5 milliseconds. The alternate and preferably fast switchover (faster, preferably much faster, than the duration of a measuring cycle) can guarantee that during a movement of the object to be examined relative to the measuring space of the computed tomograph during a single topogram scan or a single measuring cycle, the object to be examined in an image detail is measured more or less simultaneously and completely with the first and completely with the second X-ray energy. The great advantage of the method lies in the reduction in movement artifacts in the acquisition of the two-dimensional projection overview image data which can occur in particular in the region of the spine of a person or animal, for example due to breathing and/or intestinal movements during the measuring process.

A switchover is preferably made between the first X-ray energy and the second X-ray energy in a frequency such that with a movement of the object to be examined relative to the measuring space the first projection overview image partial data record and the second projection overview image partial data record acquired immediately thereafter, which have been acquired with an identical first or second X-ray energy, include projection overview image data from an identical section of the object to be examined.

A first projection overview image partial data record and a second projection overview image partial data record acquired immediately thereafter (adjacent) accordingly have an intersecting amount of data if the object to be examined was not moved in a period lying between the acquisition processes with the first or second X-ray energy. A subsequent first projection overview image partial data record in turn preferably includes projection overview image data from an identical section of the object to be examined, as it includes the preceding second projection overview image partial data record. Each projection overview image partial data record, which is acquired following a projection overview image partial data record acquired with identical first or second X-ray energy, therefore preferably includes projection overview image data from an identical section of the object to be examined.

In other words, a scan of the object to be examined is carried out with local overlappings of the respective image details. This requires matching of a speed of the movement of the examination table relative to the measuring space of the computed tomograph and a switchover frequency between the two X-ray energies. If the switchover frequency is regular during the acquisition of the projection overview image data, the speed of the movement of the examination table relative to the measuring space is preferably also constant. The particular advantage of the method lies in a simplified merging of the individual projection overview image partial data records to form an overall image data record in each case for the first and/or for the second X-ray energy by way of the possibility of overlaying the intersecting amounts of data for the purposes of comparison. In addition, any differences in the intersecting amount of data of successively acquired projection overview image partial data records, which may be caused for example by movements of the object to be examined, can be eliminated or reduced for example by automatic interpolation methods.

A low-energy image data record is preferably produced from the projection overview image partial data records acquired with the first X-ray energy and a high-energy image data record is preferably produced from the projection overview image partial data records acquired with the second X-ray energy to determine the bone overview image data record therefrom.

The low-energy and the, relative to the low-energy image data record, high-energy image data record are preferably produced with the aid of calculation methods which merge the respective underlying projection overview image partial data records separately in accordance with the X-ray energy used in each case during acquisition. The first projection overview image partial data record forming the basis of the low-energy image data record has been previously acquired with the first X-ray energy, which was preferably generated with an X-ray tube voltage between 70 kV and 100 kV. The second projection overview image partial data record forming the basis of the high-energy image data record has been previously acquired with the second X-ray energy, which was preferably generated with a tube voltage between 120 kV and 150 kV.

At least one embodiment of the inventive method for determining the bone overview image data record preferably includes registration of the low-energy image data record and the high-energy image data record on top of each other, and this optionally also includes generation of a position-corrected low-energy image data record and/or a position-corrected high-energy image data record.

During registration the low-energy and high-energy image data records can preferably be matched in such a way that different pixel values are allocated to optimally identical coordinates in the detail of the object to be examined. An allocation or overlaying of the image data records can occur by way of an orientation towards clear reference points which may be for example specific anatomical features of the object to be examined which can be localized in the two image data records. The differences in position between inner and/or outer structures of the object to be examined can be caused by a movement of individual components of the entire object to be examined and, taking the example of a person or animal, can be attributed to breathing movements and movements emanating therefrom of the torso during the measuring process(es).

If the registration process results in such differences in position being found between the low-energy and the high-energy image data records, then according to at least one embodiment of the inventive method one image data record is matched to the other by way of a position correction of the shifted structures. The adjustment can be made on the low- and/or high-energy image data record and occurs with the aid of appropriate calculation methods. The elimination of adverse movement influences of the object to be examined promotes more precise evaluation of the measurement data and more reliable determination of the bone mineral density value.

According to a preferred embodiment, a soft tissue overview image data record is produced from the low-energy image data record and the high-energy image data record or from the registered, in particular position-corrected, low-energy image data record and/or the registered, in particular position-corrected, high-energy image data record in addition to the bone overview image data record of an embodiment of the inventive method.

The soft tissue overview image data record preferably substantially includes information on outlines, thickness and material quality of the soft tissue acquired in the image detail (for example organs, muscles, tendons, vessels) of the preferably human or animal object to be examined. The information can be displayed for example by way of gray scale graduation and/or color coding and thus be made discernible to the operator. The soft tissue overview image data record can be produced by an image processing method which is based on a weighted subtraction of soft tissue image data and leads to elimination of bone structures of the object to be examined.

As an alternative to this a function can be used to calculate the soft tissue overview image data record, and this allocates a areal density value of the soft tissue to the attenuation in the high- and low-energy projection overview image data.

At least one embodiment of the inventive method makes use of the fact that the attenuation of X-ray radiation follows a material-specific and an energy-specific pattern. The material-specific attenuation behavior of the X-ray radiation enables a material breakdown and a corresponding quantitative material identification, detection and analysis. The starting point of the material breakdown are two basic materials. The basic materials are specified at the start of the breakdown or are determined by means of a reference measurement.

The step of an embodiment of the inventive method for determining a specific evaluation region in an image detail of the object to be examined preferably occurs semi- or fully automatically. The term "fully automatic" is taken to mean independent processing of defined processes according to specific programs by the computerized tomography system. The program sequence can include one or more confirmation prompts to an operator in this case as well, however. The limitation "semi-automatic" means that one or more intermediate step(s) of the program sequence can be controlled and/or modified by the operator. The program sequences can be implemented as a computer program product which is executed by an arithmetic logic unit of the computed tomograph.

The program sequences determine the evaluation region preferably by means of topographic data of human and/or animal skeletons, particularly preferably of femoral necks and/or lumbar spines and/or wrist bones, stored in a database, wherein the bone models are representative of a broad spectrum of individual bones. The evaluation region is determined following a comparison of the stored bone models with the bone overview image data record produced.

An evaluation region is preferably determined using a segmenting method. The segmenting method can take place in multiple stages, by way of example in the following two stages: a pre-segmenting step based on the entire object to be examined represented in the bone overview image data record can lead to a localization of specific bones or specific regions of a skeleton, for example the pelvic bone region. To carry out this first segmenting program module a "bounding box" by way of example can be automatically set in manner known to a person skilled in the art or by way of input via a graphic user interface, and this roughly surrounds the region which is to subsequently be selected. A second segmenting step based on the pelvic bone region can then lead to a further delimitation and isolate for example the first four vertebrae of the lumbar spine starting at the pelvic bone. The tried and tested "region growing" method by way of example, which combines homogeneous pixels to form regions and can therefore bring about identification of a specific bone portion, is suitable for carrying out this second segmenting program module. The described method proves to be particularly advantageous since an evaluation region is selected in which an optimally significant bone mineral density value can be determined. Due to the fact that an operator does not have to intervene, or only has to intervene slightly, in the segmenting process the method quickly provides reliable results.

After determination of the smallest evaluation region of the part of the object to be examined represented in the bone overview image data record the bone mineral density value is determined in this evaluation region.

A mean of a concentration of calcium hydroxylapatite is preferably calculated in the smallest examined evaluation region. A visual representation of the calcium hydroxylapatite content for the operator can be made by way of example by a gray scale graduation and/or by a color coding which correlates with the specific measured value ranges.

As already indicated above, bone density values can preferably already be directly determined as a result of a material breakdown for the bone overview image data record. In this case the bone density can be calculated in the evaluation region with the aid of a calibration function or calibration factors.

Specific reference measurement objects (calibration bodies or calibration phantoms) with different materials in a known concentration or density can be measured for this purpose.

An object with a defined calcium hydroxylapatite content (for example 200 mg Ca—Ha pro cm3 fluid) in conjunction with a water content is preferably used as a reference measurement object. A calibration of the CT system by means of the calibration phantom is enabled since the gray density values, produced with the aid of an evaluation program, in the smallest evaluation region of the bone overview image data record are converted into calcium hydroxylapatite equivalents. The gray density values for water and calcium hydroxylapatite resulting from a topogram scan of the calibration phantom form the basis for conversion for this. A corresponding bone mineral density value in the unit g Ca—Ha pro cm2 can be calculated by interpolation by means of suitable algorithms for each X-ray radiation attenuation value determined in the case of an object to be examined.

The calibration measurement can either be made in advance within the framework of routine system maintenance or during a CT scan. In the second case the calibration phantom is simultaneously scanned during the CT scan of a patients.

The first and second two-dimensional projection overview image data and the first and second projection reference image data of a reference measurement object are preferably acquired in a joint measuring cycle for determining the calibration function. This can occur for example in that the reference measurement object is placed on the examination table next to the object to be examined in such a way that it is not shielded by part of the object to be examined and is penetrated by the same intensity of X-ray radiation in each case as the object to be examined itself.

By way of direct calibration of the acquisition unit of the computed tomograph the inventive use of a reference measurement object guarantees particularly precise determining of the bone mineral density value of the object to be examined. If calibration functions are determined by means of the calibration phantom in a three-dimensional method, and this would in principle also be possible, the values have to be converted accordingly since even with the inventive method the bone mineral density values calculation are calculated on the basis of two-dimensional projection overview image data.

An embodiment of the inventive method preferably includes the step of determining bone mineral density reference values using the bone mineral density value. A bone mineral density reference value sets the absolute bone mineral density value determined on the object to be examined in relation to a bone mineral density mean which has been obtained with the aid of a statistically significant group of similar objects to be examined. If the object to be examined is a person, preferably two standardized bone mineral density means can be set in relation to the absolute bone mineral density value of the object to be examined. On the one hand this can be the bone mineral density mean of a healthy young normal population, and on the other hand the bone mineral density mean of a normal population whose average age matches the age of the object to be examined.

Alternatively or additionally, a gender-specific mean can also be set in relation to the absolute bone mineral density value. A bone mineral density reference value calculated using the first bone mineral density mean can be for example the "T score" (corresponding to a WHO definition). A bone mineral density reference value calculated using the second bone mineral density mean can be formed for example by the "Z score" (corresponding to a WHO definition). The particular advantage of the method lies in the comparability of the determined absolute bone mineral density value. If the absolute bone mineral density value differs from the first and/or the second mean outside of certain tolerances this can be a reason to initiate further processes.

At least one embodiment of the inventive method preferably includes the step of issuing a report of measurement data of the object to be examined. The report is preferably a standardized evaluation form and can be prepared for the operator by means of an output device, for example on a screen or as a printed handout and/or be stored in a memory for subsequent use. The report includes at least one detail of the determined bone mineral density value and the bone mineral density reference values. It preferably includes an identification of the smallest evaluation region of the object to be examined in a mapping of the bone overview image data record, in which evaluation region the bone mineral density value was determined. The identification can be made for example by means of colored highlighting. In addition, information about the soft tissue overview image data record may be integrated in the mapping of the bone overview image data record. Furthermore, the report can also include specific X-ray projection parameters. Issuing of the report offers the advantage of an easily comprehensible record of results for the operator and any second and third parties.

As mentioned, it is in principle possible to have an embodiment of the inventive method run fully automatically without the action of a user. The selected scan protocol is preferably transferred to an operator, however, for modification and/or confirmation, wherein confirmation or modification signals are input by the operator via an operator interface which is connected to the inventive controller or is integrated therein. This can ensure that the practical knowledge of highly trained operators is not ignored and that optionally additional fine tuning of the selected scan protocol, i.e. by way of example the modification of individual scan protocol parameters, is enabled. It is also necessary especially in the medical technology sector that staff trained in medical technology ultimately make the decision that a scan is made using a specific selected scanning method. The possibility of reconfirmation is used for this purpose.

In FIG. 1 an object to be examined, in this case a patient, is placed in a first step 1.I. on an examination table of a computerized tomography system in order to carry out imaging of the object to be examined with a specific conceptual interest. In a further step 1.II. a first topogram, i.e. a two-dimensional overview scan, of the entire object to be examined is produced, wherein the first projection overview image data PU1 forming the basis of the first topogram is obtained with a first X-ray energy of about 80 kV. Conclusions by way of example about the position, size or peculiarities of the object to be examined can be drawn from the first topogram. The creation of a topogram by means of the CT system is usually provided as part of a CT scan as standard anyway, so this method step before implementation of a computed tomography scan does not signify any additional effort. In a further step 1.III. it is queried whether in an extension of the original conceptual interest a bone density analysis of the object to be examined should be made. In the case of a decision for bone density analysis (branch "y") a second topogram of the object to be examined is produced in an identical image detail in a further step 1.IV. The second topogram in the form of second projection overview image data PU2 is obtained with a second X-ray energy of about 140 kV and in conjunction with the first topogram enables subsequent determination of a bone mineral density value KD. In the case of a decision for or against (branch "n") the bone density analysis is made in a further step 1.V. of the planned CT scan of the object to be examined.

After this step 1.V. a processing method (postprocessing) of the acquired CT and topogram measurement data begins, and this is carried out in an information processing device of the CT system or an external computing device connected to the CT system. A further query about the performance of a bone density analysis forms a further step 1.VI. if a dual energy topogram, i.e. two successive X-ray overview images produced with two different X-ray energies, has been previously produced in the described sequential method. In the case of a decision against performance of bone density analysis (branch "n") only the sectional image data of the object to be examined acquired during the CT scan is evaluated in a further step 1.VIII.B. and output to the operator. In the case of a decision for bone density analysis (branch "y") the bone mineral density value KD and further bone mineral density reference values KDB (for example T score, Z score) derived therefrom are determined in a further step 1.VII. Then the sectional image data acquired and evaluated during the CT scan is output to the operator in conjunction with the bone density analysis data in a step 1.VIII.A. which is an alternative to step 1.VIII.B. The sequential dual energy topogram, which is produced from two separate topogram acquisitions (i.e. in separate measuring cycles), is particularly suitable for the measurement of human extremities, such as a femoral neck or a wrist, since their mapping quality is barely affected by scarcely avoidable breathing movements of the test person.

FIG. 2 shows a method variant which in individual steps is identical to the procedure shown in FIG. 1. In particular all steps of the processing method (postprocessing) 2.V., 2.VI., 2.VII.A., 2.VII.B., which is carried out after acquisition of the first and optionally the second topogram(s) and the CT sectional image scans, are identical. The sequence shown in FIG. 2 differs from the sequence according to FIG. 1 primarily in that a query about performance of a bone density analysis of the object to be examined must be made as early as in a step 2.II. before execution of the first planning topogram. In the case of a decision for bone density analysis (branch "y") a simultaneous dual energy topogram is taken in a sub-step 2.III.A1, which by means of high-frequency reciprocal switchover between the first (80 kV) and second (140 kV) X-ray energy during a single measuring cycle correspondingly includes alternate first T11, T21, ..., TN1 and second T12, T22, ..., TN2 projection overview image partial data records or single image fragments.

Sub-step 2.III.A1 can include the step of acquisition of first and second projection reference image data with the two different X-ray energies from a calibration phantom, which is simultaneously scanned with the object to be examined since during the measuring process for example it is located on an examination table next to the object to be examined. The first or second projection reference image data can in this case also be recorded together with the first T11, T21, ..., TN1 and second T12, T22, ..., TN2 projection overview image partial data records in one file respectively. Due to the defined material composition and X-ray radiation attenuation properties of the calibration phantom the first and second projection reference image data are used as reference values for subsequent calculation of the bone mineral density value.

By interpolation of the single image fragments a low-energy image data record BDL can be calculated from the first projection overview image partial data records T11, T21, ..., TN1 and a, relative thereto, high-energy image data record BDH can be calculated from the second projection overview image partial data records T12, T22, ..., TN2 in a further sub-step 2.III.A2. When making a movement correction during the course of a registration process of the projection overview image partial data records a position-corrected low-energy image data record BDKL and a position-corrected high-energy image data record BDKH may be produced in the process. In contrast to the procedure shown in FIG. 1 the simultaneously acquired "dual energy topogram" (including the individual topograms for the two X-ray energies) produced in this way can be used as a planning topogram for a CT scan 2.IV. and for a subsequent bone density analysis 2.VI. of the object to be examined. Compared to a single-energy planning topogram this production of the simultaneously acquired dual energy topogram does not lead to additional time expenditure. The radiation exposure for the patient does not increase either, or increases marginally at most. The method shown in FIG. 2 is particularly suitable for determining a bone mineral density value in vertebral bodies of the human lumbar spine since the fast switchover between the two X-ray energies minimizes movement artifacts in the region of the spine owing to intestinal or breathing or other patient movements during or between the two scans.

FIG. 3 schematically shows production of a topogram scan according to the method described in FIG. 2. A fast switchover of the X-ray source between the first R1 and second R2 X-ray energy (time interval for example 0.5 milliseconds: fast kVp-switching) occurs in conjunction with a constant movement of the examination table in a direction of movement Z. A suitable ratio of switchover frequency and movement speed leads to a detector arrangement of the CT system, which usually has a multi-line sensor surface, always acquiring a plurality of projection overview image partial data records T11, T21, ..., TN1, T12, T22, ..., TN2 which include the projection image data of an identical partial area of the object to be examined. This applies to both projection overview image partial data records T11, T21, ..., TN1, which are acquired with a first, lower X-ray energy, and to projection overview image partial data records T12, T22, ..., TN2, which are obtained with a second, compared to the first X-ray energy, higher, X-ray energy. The overlapping or interleaving of the projection overview image partial data records T11, T21, ..., TN1, T12, T22, ..., TN2 illustrated schematically here in the measurement of the object to be examined with an identical and/or different X-ray energy offers the possibility of the production of more precise mappings of the object to be examined by the formation of means of the individual acquired projection overview image partial data records T11, T21, ..., TN1, T12, T22, ..., TN2 and/or by a selection of the best partial data records T11, T21, ..., TN1, T12, T22, ..., TN2 in each case.

FIG. 4 shows a method which follows the method shown in FIG. 3. The projection overview image partial data records T11, T21, ..., TN1 acquired with the first X-ray energy R1 and the projection overview image partial data records T12, T22, ..., TN2 acquired with the second X-ray energy R2 are therefore separately processed further or combined by way of an interpolation method I or suitable algorithms into a low-energy image data record BDL (topogram) and a, relative thereto, high-energy image data record BDH (topogram). The interpolation method I includes a step of averaging and/or selection in relation to a partial surface of the object to be examined which, owing to an overlapping measurement area, has been mapped in both a first T11 and a second T12 projection overview image partial data record. A selection can be made in that a program of the interpolation method I automatically recognizes and selects a qualitatively better one of two mappings of the partial surface and feeds it into a subsequent imaging processing procedure. Averaging denotes the formation of means in the comparison of two projection overview image partial data records T11, T12 which have an intersection in the form of projection image data of the same partial surface. The means can replace the original acquired projection image data and be fed into a subsequent image processing procedure.

Figure 5:
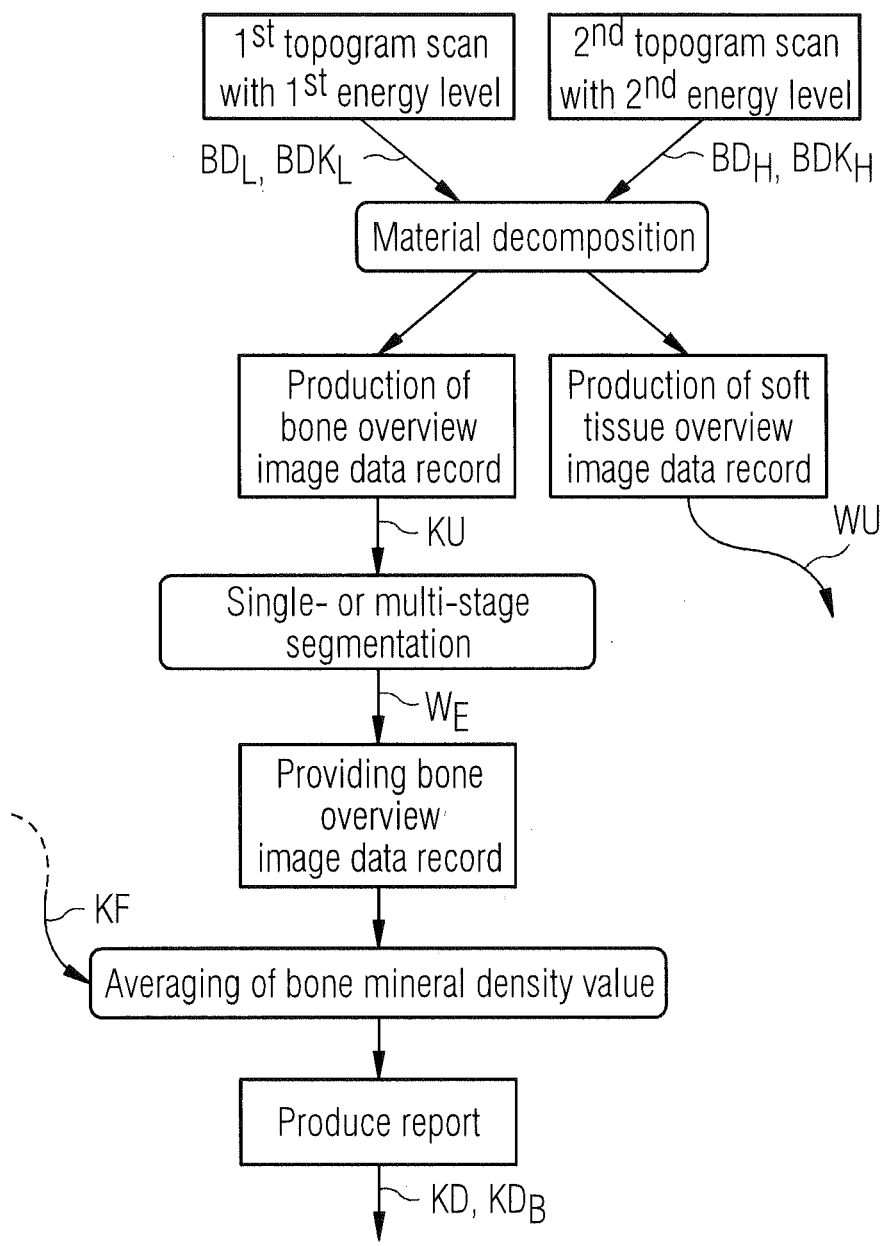
FIG. 5 shows a flowchart of a bone density analysis after acquisition of the low-energy topogram and of the high-energy topogram.

FIG. 5 shows a postprocessing procedure after the acquisition of single image fragments or projection overview image partial data records T11, T21, ..., TN1, T12, T22, ..., TN2 with the first and second X-ray energies with the aim of determining a bone mineral density value KD of the object to be examined or of the patient. In a first sub-step 5.I.A. a low-energy image data record BDL is calculated from the first projection overview image partial data records T11, T21, ..., TN1 produced with the first X-ray energy of 80 kV and in a subsequent sub-step 5.I.B. a high-energy image data record BDH is calculated from the projection overview image partial data records T12, T22, ..., TN2 produced with the second X-ray energy of 140 kV. In particular when carrying out the sequential dual energy topogram (as described in FIG. 2), the first 5.I.A. and/or second 5.I.B. sub-step(s) can include the intermediate step of a movement correction to eliminate movement artifacts. In this case a position-corrected, low-energy image data record BDKL and/or a position-corrected, high-energy image data record BDKH is produced which are fed into the continuing imaging processing procedure. A step 5.II. of material breakdown, which is known to a person skilled in the art, follows. It is based on the fact that materials of different density have a characteristic curve of the attenuation coefficient as a function of the applied X-ray energy. The absorption characteristics of a body, in particular of an organic tissue or structures embedded therein, can be taken into account during imaging as a result of the material breakdown. Due to the comparatively high calcium concentration in human and animal bone the bone overview image data record KU is obtained with the aid of X-ray radiation attenuation values of calcium. It is possible in this connection to directly allocate an areal density value in the bone overview image data record KU with the aid of a two-dimensional function to the measured attenuation in the high- and low-energy-projection overview image data.

The material breakdown results in the production of a bone overview image data record KU 5.III.A. and a soft tissue overview image data record WU 5.III.B. of the object to be examined.

The following method steps 5.IV., 5.V., 5.VI., 5.VIII. refer exclusively to the bone overview image data record KU. Firstly, a single- or multi-stage segmenting 5.IV. of the bone overview image data record KU is carried out to define a number of evaluation regions WW, WE to determine the bone mineral density value KD. A first, further evaluation region WW, can include by way of example a complete pelvic area of the patient (see FIG. 6) which can be roughly defined by a bounding box. A narrow evaluation region WE can then be segmented within the wide evaluation region WW. It preferably includes the first four vertebral bodies der lumbar spine and/or one or two femoral necks. In addition, one or two wrists can also be segmented as a narrow evaluation region WE or parts thereof.

The selection of the evaluation region follows the provision of the bone overview image data record KU with the segmented evaluation regions WE 5.V. In a further step 5.VI. the bone mineral density value KD is averaged over the segmented evaluation region WE to determine the bone mineral density value KD. If bone mineral density values KD have not already been determined in the material breakdown for the bone overview image data record KU, the image data mean is converted at this point into a physical density value in the unit calcium hydroxylapatite per cm2 fluid using a calibration function KF previously determined by means of the calibration phantom (see FIG. 2).

The bone mineral density reference values KDB (T score, Z score) are then determined based on this. In a final step 5.VII. a report is produced which includes at least one bone overview image data record KU with the segmented evaluation region(s) WW, WE, an absolute bone mineral density value KD and relative bone mineral density values or bone mineral density reference values KDB in the form of the T score and the Z score.

FIG. 6 shows a scanner 14 of a computerized tomography system 1. It is connected to an electronic control system 25 which forms a part of the CT system 1. The scanner 14 substantially includes an examination table 23 as a positioning unit for the object to be examined and a measuring space 12 around which a gantry (not shown) rotatably mounted in the scanner housing is annularly arranged with an X-ray source 2 and a detector arrangement 3 located opposite the X-ray source 2. During operation of the CT system 1 an X-ray fan beam or X-ray cone beam issuing from the X-ray source 2 runs through the measuring space 12 in the direction of the detector arrangement 3. In the case of a topography scan X-ray source 2 and detector arrangement 3 do not rotate around the measuring space, however. Instead they are each at a fixed angular position, which in the case of the X-ray source 2 is a 12 o'clock position above the examination table 23 and in the case of the detector arrangement 3 is a 6 o'clock position below the examination table 23 to produce a frontal projection of the body 17.

The examination table 23 can be moved into the measuring space 12 here. Alternatively, it is also possible to move the scanner 14 together with its housing in the direction of the examination table 23. Positioned on the examination table 23 is a body 17 of a patient as the object to be examined and a calibration phantom 19 as the reference measurement object. An image detail A includes in this connection the entire X-ray projection image or fluoroscopic image of the body 17 and of the calibration phantom 19 which in a measuring process are impinged upon by X-ray radiation from the X-ray source 2 and are measured by the detector arrangement. Basically the image detail A can, however, also include only a section of the body, for example only the lower body. A further evaluation region WW forms a section of the image detail A. Two parts of the body 17 are defined as a narrow evaluation region WE within the wide evaluation region WW here: a lumbar spine 15a and femoral neck 15b.

The control system 25 is used to carry out a tomography scan with the aid of the CT system 1. It has input and output interfaces 27, 29, 31, 33, 35, 37 via which control data SD1, SD2, SD3 is output or measurement data received. The measurement data includes the first projection overview image partial data records T11, T21, ..., TN1 and second projection overview image partial data records T12, T22, ..., TN2 acquired during a simultaneous or sequential dual energy topogram of the body 17. The measurement data also includes the first projection reference image data PR1 and the second projection reference image data PR2 acquired during a simultaneous or sequential dual energy topogram of the calibration phantom 19.

The control system 25 also includes a central inventive controller 10 arranged on a processor and a scan protocol memory 41a connected thereto. The controller 10 generates control data SD1, SD2, SD3 to control the CT system 1. Control data SD1 for controlling the detector arrangement 3 is emitted via the output interface 31. The first projection overview image partial data records T11, T21, ..., TN1 and the second projection overview image partial data records T12, T22, ..., TN2 and the first projection reference image data PR1 and the second projection reference image data PR2 pass from the detector arrangement 3 via the input interface 27 into the controller 10. This continues to generate control data SD2 which is forwarded via the output interface 29 to the X-ray source 2 to control it. Further control data SD3 passes via the output interface 33 to the positioning unit 23 for the object to be examined, whereby the advance movement thereof for example is controlled.

The controller 10 includes an image generating unit 21, a bone overview determination unit 51, an evaluation region determination unit 53 and a mineral density value determination unit 55.

The image generating unit 21 produces a low-energy image data record BDL from the first projection overview image partial data records T11, T21, . . . , TN1 and a high-energy image data record BDH from the second projection overview image partial data records T12, T22, . . . , TN2. It has a registration function, in particular performance of a position correction of the low-energy image data record BDL and the high-energy image data record BDH.

As described above, the bone overview determination unit 51 produces a bone overview image data record KU and preferably also a soft tissue overview image data record WU from the low-energy image data record BDL and the high-energy image data record BDH (optionally position-corrected).

As described above, the evaluation region determination unit 53 determines a wide evaluation region WW in the bone overview image data record KU and a narrow evaluation region WE within the wide evaluation region WW.

The mineral density value determination unit 55 calculates a bone mineral density value KD and bone mineral density reference values KDB (T score, Z score) for the narrow evaluation region WE of the segmented bone overview image data record KU.

The controller 10 is connected by a first output interface 35 to a terminal 43. Selection and control information can be input and output in interaction with an operator hereby.

A second output interface 37 is connected to a bus 45 to which a mass storage device 47 and a radiological information and imaging system 49 are connected. By way of example image data, image processing commands and further information, which is to be fed to secondary processing, storage or forwarding to further image data users, can be forwarded via the output interface 37. This includes all data calculated by the controller 10 or one of its sub-units, i.e. the low-energy image data record BDL, the high-energy image data record BDH, the position-corrected low-energy image data record BDKL, the position-corrected high-energy image data record BDKH, the bone overview image data record KU, soft tissue overview image data record WU, bone mineral density value KD, bone mineral density reference value KDB and the calibration function KF. The radiological information and imaging system 49 can therefore execute (sub-)functions of the image generating unit 21, bone overview determination unit 51, evaluation region determination unit 53 and the mineral density value determination unit 55. It can execute by way of example a segmenting method which consists of the localization of the wide evaluation region WW and of the narrow evaluation region WE, and is necessary for determining the bone mineral density value KD and bone mineral density reference values KDB. In different intermediate steps of the inventive method data records can be buffered in the mass storage device 47 and then be fed to the processing chain again by way of a data processing unit.

FIG. 6 shows only selected components of the CT system 1, which are particularly suited to illustrating the invention, and the control system 25 contained therein. Of course both devices also have a large number of further functional components.

In conclusion reference is again made to the fact that the methods described in detail above and the illustrated device are only exemplary embodiments which can be modified by a person skilled in the art in a wide variety of ways without departing from the scope of the invention. The use of the indefinite article "a" or "an" does not prevent the relevant features from also being present several times. The term "unit" similarly does not prevent this from consisting of a plurality of cooperating sub-components which may optionally also be physically separated.

What is claimed is:

1. A method for determining bone mineral density values of an object to be examined by way of a computerized tomography system, the method comprising:
    acquiring first two-dimensional projection overview image data of the object to be examined in an image detail with a first X-ray energy;
    acquiring at least second two-dimensional projection overview image data of the object to be examined in an image detail with at least one second X-ray energy, which differs from the first X-ray energy;
    planning a computerized tomography (CT) examination of the object using one of the first two-dimensional projection overview image data and the second two-dimensional projection overview image data;
    determining a bone overview image data record using the first projection overview image data and the second projection overview image data;
    determining at least one specific evaluation region of the image detail using the bone overview image data record; and
    determining a bone mineral density value for the specific evaluation region of the image detail using the image data of the bone overview image data record in the specific evaluation region such that one of the first two-dimensional projection overview image data and the second two-dimensional projection overview image data is simultaneously used to plan the CT examination and determine the bone mineral density value for the specific evaluation region of the image detail of the object.

2. The method as claimed in claim 1, wherein the acquiring of the first and second projection overview image data include;
    moving the object to be examined relative to a measuring space of the computerized tomography system;
    switching over an X-ray source between the first X-ray energy and the second X-ray energy; and
    acquiring first projection overview image partial data records with the first X-ray energy and acquiring second projection overview image partial data records with the second X-ray energy of the object to be examined in an image detail.

3. The method of claim 2, wherein the first projection overview image partial data records and the second projection overview image partial data records are acquired by way of an alternate switchover between the first X-ray energy and the second X-ray energy.

4. The method of claim 3, wherein, between the first X-ray energy and the second X-ray energy, a switchover is made in a frequency such that, with a movement of the object to be examined relative to the measuring space, the first projection overview image partial data record and second projection overview image partial data record (acquired directly thereafter, which have been acquired with an identical first or second X-ray energy, include projection overview image data of an identical section of the object to be examined.

5. The method of claim 2, further comprising:
    producing a low-energy image data record from the projection overview image partial data records acquired with the first X-ray energy, and a high-energy image data record from the projection overview image partial data records acquired with second X-ray energy, to determine the bone overview image data record.

6. The method of claim 5, wherein, to determine the bone overview image data record, the low-energy image data record and the high-energy image data record are registered on top of each other.

7. The method of claim 5, wherein, in addition to the bone overview image data record, a soft tissue overview image data record is produced from the low-energy image data record and the high-energy image data record or from at least one of the registered low-energy image data record and the registered high-energy image data record.

8. The method of claim 1, wherein the determining of a specific evaluation region occurs semi- automatically or fully automatically.

9. The method of claim 1, wherein the determining of the bone mineral density value in a specific evaluation region occurs using a calibration function.

10. The method of claim 1, wherein bone density values are determined directly as a result of a material breakdown in the bone overview image data record.

11. The method of claim 9, wherein the first and second two-dimensional projection overview image data and the first and second projection reference image data of a reference measurement object are acquired in a joint measuring cycle for determining the calibration function.

12. The method of claim 1, further comprising:
determining bone mineral density reference values using the bone mineral density value.

13. The method of claim 1, further comprising:
issuing a report of measurement data of the object to be examined.

14. A non-transitory computer readable medium including program code segments that, when executed by configure the processor to execute the method of claim 1.

15. The method of claim 3, further comprising:
producing using interpolation a low-energy image data record from the projection overview image partial data records acquired with the first X-ray energy, and a high-energy image data record from the projection overview image partial data records acquired with second X-ray energy, to determine the bone overview image data record.

16. The method of claim 4, further comprising:
producing using interpolation a low-energy image data record from the projection overview image partial data records acquired with the first X-ray energy, and a high-energy image data record from the projection overview image partial data records acquired with second X-ray energy, to determine the bone overview image data record.

17. The method of claim 6, wherein the low-energy image data record and the high-energy image data record are registered on top of each other by producing at least one of a position-corrected low-energy image data record and a position-corrected high-energy image data record.

18. A computerized tomography system, comprising:
a controller configured to,
acquire first two-dimensional projection overview image data of an object to be examined in an image detail with a first X-ray energy;
acquire second two-dimensional projection overview image data of the object with a second X-ray energy, wherein the second X-ray energy differs from the first X-ray energy;
planning a computerized tomography (CT) examination of the object using one of the first two-dimensional projection overview image data and the second two-dimensional projection overview image data;
determine a bone overview image data record using the first projection overview image data and the second projection overview image data;
determine at least one specific evaluation region of the image detail using the bone overview image data record; and
determine a bone mineral density value for the specific evaluation region of the image detail using the image data of the bone overview image data record in the specific evaluation region such that one of the first two-dimensional projection overview image data and the second two-dimensional projection overview image data is simultaneously used to plan the CT examination and determine the bone mineral density value for the specific evaluation region of the image detail of the object.

* * * * *